(12) United States Patent
Kanou et al.

(10) Patent No.: US 8,889,907 B2
(45) Date of Patent: Nov. 18, 2014

(54) PROCESS FOR PRODUCTION OF AMIDE COMPOUNDS

(75) Inventors: Makoto Kanou, Kanagawa (JP);
Kiyonobu Niwa, Kanagawa (JP);
Masahito Oda, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 94 days.

(21) Appl. No.: 12/922,376

(22) PCT Filed: Mar. 13, 2009

(86) PCT No.: PCT/JP2009/054860
§ 371 (c)(1),
(2), (4) Date: Sep. 13, 2010

(87) PCT Pub. No.: WO2009/113654
PCT Pub. Date: Sep. 17, 2009

(65) Prior Publication Data
US 2011/0021819 A1     Jan. 27, 2011

(30) Foreign Application Priority Data

Mar. 14, 2008  (JP) ................. 2008-066102

(51) Int. Cl.
*C07C 231/06* (2006.01)
*C12P 13/02* (2006.01)

(52) U.S. Cl.
CPC ..................................... *C12P 13/02* (2013.01)
USPC ........................... 564/126; 564/128; 435/129

(58) Field of Classification Search
USPC .................................. 564/126, 128; 435/129
See application file for complete search history.

(56) References Cited

U.S. PATENT DOCUMENTS

| 5,318,908 | A | 6/1994 | Seki et al. |
| 6,672,754 | B2 * | 1/2004 | Lipp ............................... 366/97 |
| 6,849,432 | B2 | 2/2005 | Abe et al. |
| 7,597,115 | B2 * | 10/2009 | Lothe ............................. 137/592 |
| 2008/0311645 | A1 | 12/2008 | Higashiyama |

FOREIGN PATENT DOCUMENTS

| EP | 1352965 A1 | 10/2003 |
| EP | 1835033 A1 | 9/2007 |
| JP | 2-177883 A | 7/1990 |
| JP | 11-89575 A | 4/1999 |
| JP | 2001-340091 A | 12/2001 |
| JP | 2006-61039 A | 3/2006 |
| JP | 2006-67964 A | 3/2006 |
| WO | 02/50297 A1 | 6/2002 |
| WO | 03/000914 A1 | 1/2003 |
| WO | WO 2005/054456 | * 6/2005 |
| WO | WO 2006/007957 | * 1/2006 |

* cited by examiner

*Primary Examiner* — Shailendra Kumar
(74) *Attorney, Agent, or Firm* — McDermott Will & Emery LLP

(57) ABSTRACT

The present invention provides a method for producing an amide compound from a nitrile compound using a biocatalyst that realizes low cost, energy saving and low environmental burdens. The production method of the amide compound of the present invention is a method for producing an amide compound from a nitrile compound using a biocatalyst in a reactor, wherein the nitrile compound is reacted with the biocatalyst to produce the amide compound under such stirring conditions that the stirring power requirement is in the range of 0.08 to 0.7 kW/m$^3$.

6 Claims, No Drawings

PROCESS FOR PRODUCTION OF AMIDE COMPOUNDS

CROSS REFERENCE TO PRIOR APPLICATIONS

This application is a U.S. National Phase application under 35 U.S.C. §371 of International Application No. PCT/JP2009/054860, filed on Mar. 13, 2009 and claims benefit of priority to Japanese Patent Application No. 2008-066102, filed on Mar. 14, 2008. The International Application was published in Japanese on Sept. 17, 2009 as WO 2009/113654 A1 under PCT Article 21(2). All of these applications are herein incorporated by reference.

TECHNICAL FIELD

The present invention relates to a method for producing an amide compound from a nitrile compound using a biocatalyst.

BACKGROUND ART

A method for producing a compound of interest utilizing a biocatalyst has advantages that reaction conditions are mild, that the purity of a reaction product is high with a small amount of a by-product, and that a production process can be simplified. Therefore, such a method is used for many compounds to be produced. In the case of production of an amide compound, since nitrile hydratase, which is an enzyme for converting a nitrile compound into an amide compound, was found, biocatalysts have been widely used.

In the industrial utilization of such a biocatalyst, it is important to make efforts toward low cost, energy saving and reduction of environmental burdens.

In order to make efforts toward low cost in the production of an amide compound, for example, the following methods are used: a method in which a microbial cell that highly expresses the nitrile hydratase activity is used in a reaction without being subjected to entrapping immobilization (Patent Document 1); a method of continuous production in which a temperature of a reaction tank downstream is high (Patent Document 2); a method utilizing a plug flow reaction (Patent Document 3); and a method in which the acrylonitrile concentration in an aqueous vehicle at the time of reaction is equal to or higher than the saturating concentration (Patent Document 4).

Patent Document 1 International Publication WO 02/050297 pamphlet
Patent Document 2 International Publication WO 03/00914 pamphlet
Patent Document 3 Japanese Laid-Open Patent Publication No. 2001-340091
Patent Document 4 Japanese Laid-Open Patent Publication No. H11-89575

DISCLOSURE OF THE INVENTION

Problems to be Solved by the Invention

However, when using any of the methods in Patent Documents 1-4, there are cases where effects on low cost, energy saving and reduction of environmental burdens are insufficient.

Under such circumstances, it has been desired to provide a method for producing an amide compound from a nitrile compound using a biocatalyst that realizes low cost, energy saving and low environmental burdens.

Means for Solving the Problems

The present invention was made in consideration of the above-described circumstances, and provides a method for producing an amide compound as described below.

A method for producing an amide compound from a nitrile compound using a biocatalyst in a reactor, wherein the nitrile compound is reacted with the biocatalyst to produce the amide compound under such stirring conditions that the stirring power requirement is in the range of 0.08 to 0.7 $kW/m^3$.

Examples of the production method of the present invention include a method in which the reaction is a continuous reaction.

Further, in the production method of the present invention, the stirring can be performed, for example, with the Froude number of 0.05 to 0.20.

The production method of the present invention is preferably applied, for example, to the production of acrylamide.

Advantageous Effect of the Invention

According to the production method of the present invention, an amide compound can be produced from a nitrile compound in an energy-saving manner with a low cost, and in addition, environmental burdens can be reduced.

BEST MODES FOR CARRYING OUT THE INVENTION

Hereinafter, the production method of the amide compound of the present invention will be described in detail. The scope of the present invention is not limited to the description. In addition to the following examples, the present invention can be suitably changed and then practiced within a range in which the effects of the present invention are not reduced.

Note that the entire specification of Japanese Patent Application No. 2008-066102 (filed on Mar. 14, 2008), to which priority is claimed by the present application, is incorporated herein. In addition, all the publications such as prior art documents, laid-open publications, patents and other patent documents cited herein are incorporated herein by reference.

The production method of the amide compound of the present invention is a method for producing an amide compound using a biocatalyst, wherein a nitrile compound is reacted with the biocatalyst to produce the amide compound under specific stirring conditions.

The production method of the present invention may be a method in which a continuous reaction is performed (a method for continuously producing an amide compound) or a method in which a batch reaction is performed (a method for discontinuously producing an amide compound), and is not limited. However, the method in which a continuous reaction is performed is preferred.

In this regard, the method in which a continuous reaction is performed means a method for continuously producing an amide compound by continuously or intermittently supplying reaction raw materials (including a biocatalyst and a nitrile compound) and continuously or intermittently taking out a reaction mixture (including the produced amide compound) without taking out the total amount of the reaction mixture in the reactor.

Examples of the biocatalyst that can be used in the production method of the present invention include an animal cell, plant cell, organelle, bacterial cell (living cell or dead cell), and treated products thereof, all of which contain an enzyme for catalyzing a reaction of interest. Examples of the treated products include a crude enzyme or purified enzyme extracted from a cell, and a product in which an animal cell, plant cell, organelle, bacterial cell (living cell or dead cell) or enzyme itself is immobilized using the entrapping method, cross-linking method, carrier binding method or the like.

Note that the entrapping method is a method in which a bacterial cell or enzyme is enclosed with a fine lattice of polymer gel or coated with a semipermeable polymer membrane. The cross-linking method is a method in which an enzyme is crosslinked with a reagent having 2 or more functional groups (polyfunctional crosslinking agent). The carrier binding method is a method in which an enzyme is bound to a water-insoluble carrier.

Examples of immobilization carriers to be used for immobilization include glass beads, silica gel, polyurethane, polyacrylamide, polyvinyl alcohol, carrageenan, alginic acid, agar and gelatin.

Examples of the bacterial cells include microorganisms belonging to Nocardia, Corynebacterium, Bacillus, Pseudomonas, Micrococcus, Rhodococcus, Acinetobacter, Xanthobacter, Streptomyces, Rhizobium, Klebsiella, Enterobavter, Erwinia, Aeromonas, Citrobacte, Achromobacter, Agrobacterium and Pseudonocardia.

Examples of enzymes include nitrile hydratase produced by the aforementioned microorganisms.

The amount of the biocatalyst to be used varies depending on the type and form of the biocatalyst to be used and the nitrile compound, but it is preferably adjusted so that the activity of the biocatalyst introduced into a reactor becomes about 50 to 200 U per 1 mg of dried cell at reaction temperature of 10° C. Note that the aforementioned unit "U" means that the amide compound is produced from the nitrile compound in an amount of 1 micromole for 1 minute, and the value is measured using the nitrile compound to be used in the production.

The nitrile compound to be used in the production method of the present invention is a compound that is converted into an amide compound by a reaction with the aforementioned biocatalyst (in other words, a compound that is hydrated in the presence of the aforementioned biocatalyst to be converted into an amide compound). Examples thereof include: aliphatic saturated nitrile such as acetonitrile, propionitrile, succinonitrile and adiponitrile; aliphatic unsaturated nitrile such as acrylonitrile and methacrylonitrile, aromatic nitrile such as benzonitrile and phthalodinitrile; and heterocyclic nitrile such as 3-cyanopyridine and 2-cyanopyridine.

The amount of the nitrile compound to be used varies depending on the type and form of the biocatalyst to be used and the nitrile compound, but it is preferred that the concentration thereof to be introduced into a reactor is about 0.5 to 5.0% by mass.

When the production method of the present invention is carried out by a continuous reaction, the fluid velocity at the time of taking out the reaction mixture from a reactor may be determined in accordance with the introduction rate of the nitrile compound, raw material water and biocatalyst so that continuous production can be carried out without taking out the total amount of the reaction mixture in the reactor.

The production method of the present invention is a method for producing an amide compound using the aforementioned biocatalyst, and examples of amide compounds to be produced include acrylamide, nicotinamide, 5-cyanovaleroamide and methacrylamide. In particular, the method of the present invention is preferably applied to the production of acrylamide.

In the production method of the present invention, in addition to the aforementioned nitrile compound, raw material water and biocatalyst, reaction raw materials comprising salts, etc. required for the reaction are introduced into the reactor, and the reaction is performed with stirring, thereby producing the amide compound from the nitrile compound. The stirring is carried out under such conditions that the stirring power requirement per unit volume of the reaction solution fluid is in the range of 0.08 to 0.7 kW/m$^3$.

In this regard, the stirring power requirement means a power consumed by an electrically-driven machine (motor) for stirring. Note that the stirring power requirement can be calculated based on a load torque generated at the axis of a stirring blade.

Further, the reaction solution fluid is a mixed solution for producing an amide compound from a nitrile compound. It means a reaction raw material at the time of initiating a reaction, and means a reaction mixture of the reaction raw material and the produced amide compound during the reaction.

When the aforementioned stirring power requirement is 0.08 kW/m$^3$ or more, the contact and dispersibility between the nitrile compound and the biocatalyst are improved, and the efficiency of conversion from the nitrile compound into the amide compound is increased. Moreover, reduction of heat-transfer performance in the reactor can be suppressed, temperature controllability of the reaction solution is improved, and energy consumption of a cooler is decreased. Meanwhile, when the stirring power requirement is 0.7 kW/m$^3$ or less, deterioration of the biocatalyst can be suppressed, and the efficiency of conversion from the nitrile compound into the amide compound is increased.

The aforementioned stirring power requirement is preferably 0.08 to 0.7 kW/m$^3$, and more preferably 0.1 to 0.4 kW/m$^3$.

Further, in the stirring in the production method of the present invention, the stirring power requirement may be changed during the reaction within the aforementioned range as long as it is within the range in which the efficiency of conversion from the nitrile compound into the amide compound, temperature controllability of the reaction solution, etc. are not reduced too much.

However, when the tip speed of the stirring blade (circumferential speed of the blade tip) is high, a big shear force is applied to the reaction solution fluid around the stirring blade, and there is a possibility that the introduced biocatalyst may be damaged to prevent an efficient reaction. Therefore, the stirring is preferably performed with the tip speed of 4.0 m/s or less.

Regarding the reactor in the production method of the present invention, one or a plurality of reactors may be used.

The type of the reactor is not limited as long as fluids in the reactor are mixed by stirring. Examples of the reactor include a tank-type reactor and a tower-type reactor.

Further, the form of the stirring blade is not limited, and examples of the stirring blade include a paddle, disk turbine, propeller, helical ribbon, anchor, pfaudler blade and fan turbine.

The stirring in the production method of the present invention is not limited, but it is performed with the Froude number of preferably 0.05 to 0.20, and more preferably 0.08 to 0.16.

In this regard, the Froude number (Fr) means a ratio between the inertial force of the reaction solution fluid and the gravity, and is a dimensionless number that affects turbulence of the interface between the liquid surface and the gas phase portion. The smaller the Froude number is, the more the interface is close to the static condition without stirring, and the larger the Froude number is, the more the turbulence of the interface is increased. The Froude number can be represented by the following formula (for example, see Maruzen, Chemical Engineering Handbook, 6th revised edition, page 424, Table 1):

$$Fr = n^2 d/g$$

(In the formula, n represents a rotational speed [1/s], d represents a stirring blade diameter [m], and g represents a gravity acceleration [m/s$^2$].)

In the production method of the present invention, when the aforementioned

Froude number is smaller than 0.05, the interface is close to the static condition. In this case, not only the dispersion of the nitrile compound in the reaction solution fluid becomes insufficient, but also the nitrile compound, whose specific gravity is small, floats near the interface. As a result, the nitrile compound is prone to be easily leaked to the gas phase portion. Meanwhile, when the Froude number is larger than 0.20, the turbulence of the interface is increased, and the contact area of the gas-liquid interface is significantly increased. As a result, leakage of the nitrile compound to the gas phase portion is accelerated.

The reaction temperature in the production method of the present invention is preferably 15 to 40° C., and more preferably 20 to 35° C. When the reaction temperature is 30° C. or higher, the reaction activity of the biocatalyst can be sufficiently increased. When the reaction temperature is 25° C. or lower, it becomes easier to suppress deactivation of the biocatalyst.

When using a plurality of reactors in the production method of the present invention, the reaction temperatures in the reactors are within the aforementioned range, and the reaction temperature in a downstream reactor from which the reaction mixture is taken out is preferably higher than the reaction temperature in an upstream reactor into which the nitrile compound and the biocatalyst are introduced. The productivity can be improved thereby.

A method for controlling the reaction temperature is not particularly limited. Examples thereof include a method using a reactor equipped with a jacket, cooling or heating coil, cooling apparatus with external circulation, heating apparatus with external circulation or the like, and a method in which the entire reactor or a part thereof is put into a constant temperature tank. Further, when using a plurality of reactors, it is possible to use a method in which a heat exchanger is inserted between the reactors.

When continuously performing a reaction using a plurality of reactors, the reactor into which the biocatalyst and the nitrile compound are to be introduced is not limited to the most upstream reactor, and the materials may also be introduced into a reactor downstream thereof, as long as it is within a range in which efficiency of the reaction, etc. are not reduced too much.

According to the production method of the present invention described above, it is possible to efficiently produce the amide compound from the nitrile compound in an energy-saving manner with a low cost.

It is thought that this is because contact between the biocatalyst and the nitrile compound, which are continuously introduced into the reactor, and dispersion thereof can be improved by stirring. Further, it is thought that this is also affected by the fact that the temperature controllability of the reaction solution is improved by stirring.

Further, it was found that, in the production method of the present invention, the stirring power requirement at the time of stirring affects not only the efficiency of conversion from the nitrile compound into the amide compound, but also leakage of the nitrile compound to the reactive gas phase portion. For example, when the stirring power requirement is more than 1.3 kW/m$^3$, not only the efficiency of conversion from the nitrile compound to the amide compound is reduced, but also leakage of the nitrile compound to the reactive gas phase portion is increased. Such leakage of the nitrile compound to the reactive gas phase portion causes not only increase in industrial production cost, but also defects such as increase in environmental burdens.

Thus, since the stirring power requirement is in the range of 0.08 to 0.7 kW/m$^3$ in the production method of the present invention, environmental burdens can be kept at low levels.

EXAMPLES

Hereinafter, the present invention will be more specifically described by way of working examples and comparative examples. However, the present invention is not limited only to these examples.

Example 1

(Preparation of Biocatalyst)

Rhodococcus rhodochrous J1 having nitrile hydratase activity (Accession number FERM BP-1478; deposited to International Patent Organism Depositary, National Institute of Advanced Industrial Science and Technology (Chuo 6, Higashi 1-1-1, Tsukuba-shi, Ibaraki) on Sep. 18, 1987) was aerobically cultured in a medium containing 2% glucose, 1% urea, 0.5% peptone, 0.3% yeast extract and 0.05% cobalt chloride (% by mass in each case) (pH 7.0) at 30° C. Using a centrifuge and 50 mM phosphate buffer (pH 7.0), the obtained culture was subjected to harvest and washing, thereby obtaining a bacterial cell suspension (dried cell: 15% by mass).

(Production of Acrylamide)

Four reaction tanks equipped with a jacket cooler (inner diameter of the tank: 0.8 m, height: 1.4 m) were serially connected.

51.1 L/hr of 50 mM phosphate buffer (pH 7.0), 27.1 L/hr of acrylonitrile and 230 g/hr of bacterial cell suspension were continuously added to the first tank, and only 11.6 L/hr of acrylonitrile was continuously added to the second tank. The amount of the reaction solution in each of the first to fourth tanks was adjusted to 500 L, and temperature control was performed using cooling water (10° C.) in the jackets so that the reaction solution temperatures in the first tank to the fourth tank became 22° C., 23° C., 24° C. and 25° C., respectively. Using a 2-blade paddle (blade diameter: 350 mm, blade width: 100 mm), the stirring power per reaction solution fluid in each of the first to fourth reaction tanks was adjusted to 0.08 kW/m$^3$ (Froude number: 0.057). Note that the stirring power requirement per reaction solution fluid was calculated by dividing the stirring power requirement in each of the reactors by the liquid measure (500 L=0.5 m$^3$).

4 days after the initiation of the reaction, the reaction solution flowing out from the fourth tank was measured by gas chromatography (column: manufactured by Waters, PoraPak-PS, 1 m, 180° C., carrier gas: helium, detector: FID).

As a result, unreacted acrylonitrile was not detected, and 50.5% of acrylamide was detected.

Example 2

A reaction was performed in a manner similar to that in Example 1, except that a 4-blade paddle (blade diameter: 300 mm, blade width: 100 mm) was used and that the stirring power requirement was set at 0.7 kW/m³ (Froude number: 0.200)

4 days after the initiation of the reaction, the reaction solution flowing out from the fourth tank was measured by gas chromatography (column: manufactured by Waters, PoraPak-PS, 1 m, 180° C., carrier gas: helium, detector: FID). As a result, unreacted acrylonitrile was not detected, and 50.5% of acrylamide was detected.

Comparative Example 1

A reaction was performed in a manner similar to that in Example 1, except that a 2-blade paddle (blade diameter: 230 mm, blade width: 100 mm) was used and that the stirring power requirement was adjusted to 0.02 kW/m³ (Froude number: 0.053).

One day after the initiation of the reaction, the temperatures in the first and second tanks were elevated to 24° C. and 25° C., respectively, and therefore, the temperature of cooling water in the jackets was decreased to 3° C.

5 days after the initiation of the reaction, the reaction solution flowing out from the fourth tank was measured by gas chromatography. As a result, 1.1% of unreacted acrylonitrile and 48.0% of acrylamide were detected. Based on the result, it was understood that acrylonitrile in an amount corresponding to about 2% of the adding amount of acrylonitrile leaked out to the reactive gas phase portion.

Comparative Example 2

A reaction was performed in a manner similar to that in Example 1, except that a 4-blade paddle (blade diameter: 450 mm, blade width: 100 mm) was used and that the stirring power requirement was adjusted to 1.32 kW/m³ (Froude number: 0.154).

4 days after the initiation of the reaction, the reaction solution flowing out from the fourth tank was measured by gas chromatography. As a result, 0.5% of unreacted acrylonitrile and 46.5% of acrylamide were detected. Based on the result, it was understood that acrylonitrile in an amount corresponding to 6% or more of the adding amount of acrylonitrile leaked out to the reactive gas phase portion.

Comparative Example 3

A reaction was performed in a manner similar to that in Example 1, except that a 6-blade paddle (blade diameter: 450 mm, blade width: 150 mm) was used and that the Froude number was set at 0.014.

4 days after the initiation of the reaction, the reaction solution flowing out from the fourth tank was measured by gas chromatography. As a result, 0.04% of unreacted acrylonitrile and 49.4% of acrylamide were detected. Based on the result, it was understood that acrylonitrile in an amount corresponding to about 2% of the adding amount of acrylonitrile leaked out to the reactive gas phase portion.

Comparative Example 4

A reaction was performed in a manner similar to that in Example 1, except that a 2-blade paddle (blade diameter: 230 mm, blade width: 50 mm) was used and that the Froude number was set at 0.235.

4 days after the initiation of the reaction, the reaction solution flowing out from the fourth tank was measured by gas chromatography. As a result, 0.02% of unreacted acrylonitrile and 48.2% of acrylamide were detected. Based on the result, it was understood that acrylonitrile in an amount corresponding to about 4.5% of the adding amount of acrylonitrile leaked out to the reactive gas phase portion.

Comparative Example 5

A reaction was performed in a manner similar to that in Example 2, except that two 6-blade paddles (blade diameter: 450 mm, blade width: 150 mm) were attached and that the Froude number was set at 0.044.

4 days after the initiation of the reaction, the reaction solution flowing out from the fourth tank was measured by gas chromatography. As a result, 0.03% of unreacted acrylonitrile and 49.5% of acrylamide were detected. Based on the result, it was understood that acrylonitrile in an amount corresponding to about 1.5% of the adding amount of acrylonitrile leaked out to the reactive gas phase portion.

Comparative Example 6

A reaction was performed in a manner similar to that in Example 2, except that two 6-blade paddles (blade diameter: 230 mm, blade width: 50 mm) were attached and that the Froude number was set at 0.261.

4 days after the initiation of the reaction, the reaction solution flowing out from the fourth tank was measured by gas chromatography. As a result, 0.02% of unreacted acrylonitrile and 48.4% of acrylamide were detected. Based on the result, it was understood that acrylonitrile in an amount corresponding to about 4.1% of the adding amount of acrylonitrile leaked out to the reactive gas phase portion.

The results of the above-described Examples and Comparative Examples regarding the stirring power requirement (per unit volume of the reaction solution fluid), Froude number, analysis of the reaction solution taken out from the reactor, temperature controllability and leakage of the nitrile compound to the reactive gas phase portion are shown in Table 1 below.

TABLE 1

| | Stirring power requirement [kW/m³] | Froude number [-] | Detection [%] | | Temperature controllability | Leakage of acrylonitrile to the reactive gas phase portion |
|---|---|---|---|---|---|---|
| | | | Acrylonitrile | Acrylamide | | |
| Example 1 | 0.08 | 0.057 | 0 | 50.5 | ○ | Absent |
| Example 2 | 0.70 | 0.200 | 0 | 50.5 | ○ | Absent |
| Comparative Example 1 | 0.02 | 0.053 | 1.1 | 48.0 | X | Absent |
| Comparative Example 2 | 1.32 | 0.154 | 0.5 | 46.5 | ○ | Present |
| Comparative Example 3 | 0.08 | 0.014 | 0.04 | 49.4 | ○ | Present |

TABLE 1-continued

| | Stirring power requirement [kW/m³] | Froude number [-] | Detaction [%] Acrylonitrile | Detaction [%] Acrylamide | Temperature controllability | Leakage of acrylonitrile to the reactive gas phase portion |
|---|---|---|---|---|---|---|
| Comparative Example 4 | 0.08 | 0.235 | 0.02 | 48.2 | ○ | Present |
| Comparative Example 5 | 0.70 | 0.044 | 0.02 | 49.7 | ○ | Present |
| Comparative Example 6 | 0.70 | 0.261 | 0.02 | 48.4 | ○ | Present |

As shown in Table 1, in Examples 1 and 2 using the production method of the present invention, the reaction was performed while stirring with the stirring power requirement per unit volume of the reaction solution fluid being set at 0.08 to 0.7 kW/m³. Therefore, no unreacted nitrile compound was detected, and the amide compound was efficiently produced. In addition, good controllability of the reaction temperature was achieved.

Meanwhile, in Comparative Example 1, the stirring power requirement per unit volume of the reaction solution fluid was 0.02 kW/m³. Therefore, the unreacted nitrile compound was detected, and the production efficiency of the amide compound was lower than those in the Examples. In addition, temperature controllability of the reaction solution was poor.

In Comparative Example 2, the stirring power requirement per unit volume of the reaction solution fluid was 1.3 kW/m³. Therefore, the unreacted nitrile compound was detected, and the production efficiency of the amide compound was lower than those in the Examples. In addition, the nitrile compound leaked out to the reactive gas phase portion, and as a result, the effect of reducing environmental burdens was lower.

In Comparative Examples 3-6, the Froude number was not within the range of 0.05 to 0.2. Therefore, the nitrile compound leaked out to the reactive gas phase portion, and the effect of reducing environmental burdens was lower.

Thus, the production method of the amide compound of the present invention provides good efficiency of conversion from the nitrile compound into the amide compound and good temperature controllability of the reaction solution. Therefore, the amide compound was successfully produced in an energy-saving manner with a low cost. In addition, it was confirmed that leakage of the nitrile compound to the reactive gas phase portion was suppressed and that environmental burdens were low.

INDUSTRIAL APPLICABILITY

According to the production method of the present invention, at the time of producing an amide compound using a biocatalyst, the rate of conversion from a nitrile compound to the amide compound can be easily increased, and temperature at the time of reaction can be easily controlled. In addition, it is possible to prevent leakage of the nitrile compound to the outside of the reaction system. Therefore, the method can be suitably used as a method for producing an amide compound that realizes low cost, energy saving and low environmental burdens.

The invention claimed is:

1. A method for producing an amide compound from a nitrile compound using a biocatalyst in a reactor, wherein the nitrile compound is reacted with the biocatalyst to produce the amide compound in a continuous reaction under such stirring conditions that the stirring power requirement is in the range of 0.08 to 0.7 kW/m³, the Froude number is in the range of 0.05 to 0.20, and the stirring is performed with a stirring blade tip speed of 4.0 m/s or less, and wherein the biocatalyst is selected from a bacterial cell and treated products thereof.

2. The method according to claim 1, wherein the amide compound is acrylamide and the nitrile compound is acrylonitrile.

3. The method according to claim 1, wherein the bacterial cell is selected from microorganisms belonging to *Nocardia, Corynebacterium, Bacillus, Pseudomonas, Micrococcus, Rhodococcus, Acinetobacter, Xanthobacter, Streptomyces, Rhizobium, Klebsiella, Enterobavter, Erwinia, Aeromonas, Citrobacte, Achromobacter, Agrobacterium* and *Pseudonocardia*.

4. The method according to claim 1, wherein the bacterial cell is *Rhodococcus rhodochrous* J1.

5. The method according to claim 1, wherein the Froude number is in the range of 0.08 to 0.16.

6. The method of claim 1 further comprising a reaction temperature of 15° C. to 40° C.

* * * * *